United States Patent [19]
Paeth et al.

[11] Patent Number: 5,191,886
[45] Date of Patent: Mar. 9, 1993

[54] MULTIPLE ELECTRODE STRIP

[75] Inventors: David S. Paeth, Seattle; Stephen W. Gross, Snohomish; Thomas D. Lyster, Bothell, all of Wash.

[73] Assignee: Physio-Control Corporation, Redmond, Wash.

[21] Appl. No.: 687,302

[22] Filed: Apr. 18, 1991

[51] Int. Cl.$^5$ .............................. A61B 5/0402
[52] U.S. Cl. ................................................ 128/640
[58] Field of Search .................. 128/635–641, 128/644, 783, 791–793, 798, 799, 802, 803, 384, 385, 388, 389

[56] References Cited

U.S. PATENT DOCUMENTS

| | | | |
|---|---|---|---|
| 1,637,829 | 8/1927 | Lurie | 128/802 |
| 3,300,572 | 1/1967 | Dahlgren et al. | 174/69 |
| 3,572,322 | 3/1971 | Wade | 128/640 |
| 3,805,769 | 4/1974 | Sessions | 128/2.06 E |
| 4,026,278 | 5/1977 | Ricketts et al. | 128/644 |
| 4,063,352 | 12/1977 | Bevilacqua | 29/630 R |
| 4,082,086 | 4/1978 | Page et al. | 128/2.06 E |
| 4,121,575 | 10/1978 | Mills et al. | 128/2.06 E |
| 4,328,814 | 5/1982 | Arkans | 128/640 |
| 4,334,542 | 6/1982 | Takinishi et al. | 128/642 |
| 4,353,372 | 10/1982 | Ayer | 128/640 |
| 4,365,634 | 12/1982 | Bare et al. | 128/640 |
| 4,393,584 | 7/1983 | Bare et al. | 29/877 |
| 4,398,545 | 8/1983 | Wilson | 128/798 |
| 4,422,461 | 12/1983 | Glumac | 128/798 |
| 4,522,211 | 6/1985 | Bare et al. | 128/640 |
| 4,583,549 | 4/1986 | Manoli | 128/640 |
| 4,633,879 | 1/1987 | Ong | 128/641 |
| 4,635,642 | 1/1987 | Cartmell et al. | 128/639 |
| 4,638,807 | 1/1987 | Ryder | 128/644 |
| 4,669,479 | 6/1987 | Dunseath, Jr. | 128/640 |
| 4,690,148 | 9/1987 | Hess | 128/639 |
| 4,751,928 | 6/1988 | Hallon et al. | 128/644 |
| 4,763,660 | 8/1988 | Kroll et al. | 128/640 |
| 4,798,642 | 1/1989 | Craighead et al. | 156/252 |
| 4,852,572 | 8/1989 | Nakahashi et al. | 128/640 |
| 4,854,323 | 8/1989 | Rubin | 128/644 |
| 4,865,039 | 9/1989 | Dunseath, Jr. | 128/640 |
| 4,957,109 | 9/1990 | Groeger et al. | 128/640 |

FOREIGN PATENT DOCUMENTS

| | | | |
|---|---|---|---|
| 3346866 | 7/1985 | Fed. Rep. of Germany. | |
| 2531330 | 2/1984 | France | 128/644 |
| 1158163 | 5/1985 | U.S.S.R. | 128/644 |

*Primary Examiner*—Lee S. Cohen
*Attorney, Agent, or Firm*—Christensen, O'Connor, Johnson & Kindness

[57] ABSTRACT

Disclosed is an electrode strip (10) for use in electrocardiography comprising a flexible and substantially inextendible substrate (14), a plurality of conductive leads (16) and an insulating cover layer (17) including a plurality of apertures (24) therethrough. The conductive leads extend from a connector (22) to different ones of the apertures to form electrode sites (26). A plurality of regions of extensibility (30) in the strip allow selective positioning of the apertures on a body.

24 Claims, 7 Drawing Sheets

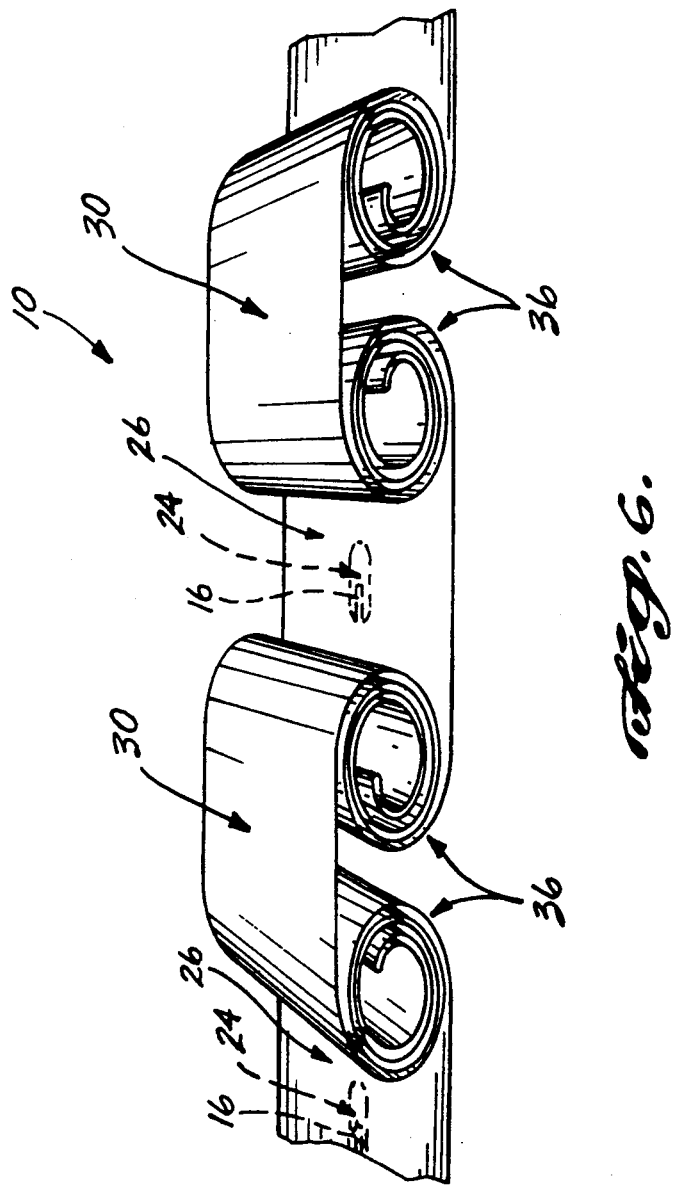

MULTIPLE ELECTRODE STRIP

FIELD OF THE INVENTION

The invention relates to monitoring systems and, in particular, to an electrode strip for use in monitoring electrical activities of a living body.

BACKGROUND OF THE INVENTION

Conventional electrocardiography is concerned with the measurement and analysis of voltage potential readings taken from a limited number of anatomically defined locations. The voltages between various locations are combined to form electrocardiograph (ECG) leads that are represented as waveforms and are compared to clinically developed criteria to diagnose or classify the state of a person's heart. One type of conventional electrocardiographic system has focused on the application of ten electrodes to a person's skin; six across the precordial or chest area of the person and one on each of the arms and legs. The electrodes are commonly attached to the body by a conductive gel within an adhesive structure, or by a gel which is both conductive and adhesive.

More recently, electrocardiologists have been experimenting with a body surface potential mapping technique as a tool in scientific investigations and in improving clinical diagnosis of heart disease. In body surface potential mapping, a large number of electrodes are applied to a person's torso to obtain an estimate of the total body surface distribution of cardiac-generated potentials. This distribution is commonly displayed as a series of isopotential contours plotted on a map that represents the person's torso. The resultant isopotential map is then evaluated for the presence of features representing the particular cardiac characteristic of interest.

Proper electrode placement is a major concern in electrocardiography. More particularly, to allow a person's ECG data to be meaningfully compared to clinical data obtained from known populations, the electrode readings must be made at uniformly defined, anatomical locations. Proper placement poses difficulties, in part, because the electrodes must be positioned on people of different sizes. In body surface mapping, the desired electrode sites are arranged in a number of columns and rows, with some mapping systems utilizing as many as 240 body surface electrodes. Thus, proper electrode placement may be further complicated by the large number of electrodes to be attached.

In an attempt to alleviate electrode placement problems, a number of electrocardiograph electrode systems have been developed. One type of system simply uses individual electrodes whose relative positions are unconstrained by the separate and distinct conductive wires that couple the electrodes to a cable that is connected to monitoring equipment. Thus, this system allows individual positioning of the electrodes upon the subject person. A second type of system provides a number of electrodes directly attached to a cable, with differently proportioned electrode-cable sets used with different-sized bodies. Other systems implement a cable or harness whereby individual electrodes attached thereto can be selectively positioned along the cable or harness structure. In one device, the electrodes are connected with spring clips to the harness allowing individual electrodes to be slidingly positioned along the harness.

The electrode arrangements described above are generally cumbersome to use and are often relatively expensive. The time required for proper placement with the more cumbersome prior art systems can be particularly important in emergency situations or when a large number of electrodes are required, for example, to perform body surface mapping. Care must be exercised with a system utilizing a separate lead for each individual electrode so that individual electrodes do not become entangled, a problem that can increase the chance that any given electrode will be placed in the wrong position, particularly in emergency situations. If differently sized electrode-cable sets are to be used to compensate for differences in body sizes, an electrocardiologist must have electrode-cable sets of several sizes at his or her fingertips. More important, the person charged with placement of electrodes is also required to select the proper size and accurately place the electrodes onto the body in a minimum amount of time. Even then, the electrode-cable set selected may not allow accurate electrode placement on persons between two sizes or at each end of the spectrum of average-sized bodies. Devices utilizing a scheme whereby the individual electrodes can be slidably positioned along an electrode cable or harness are disadvantageous in their bulk and complexity, and again, are not particularly well suited for body surface potential mapping because of the large number of electrodes required.

As can be seen, there is a continuing need to provide an electrode device which allows accurate and timely placement of individual electrodes on the body of a person, whether it be conventional electrocardiography or a technique utilizing body surface potential mapping, while reducing the complexity and cost of the device.

SUMMARY OF THE INVENTION

An electrode strip in accordance with the present invention is a unitary strip for measuring the activities of the heart or other bioelectrical events of a body while still providing a degree of flexibility in the positioning of individual electrodes. A plurality of regions of extensibility in the strip provide adaptive spacing between electrodes. The electrode strip is a disposable alternative to costlier and less manageable cables known in the art. In addition, the design of the strip allows a number of electrode strips to be simultaneously and conveniently placed on a patient for use in applications such as body surface potential mapping.

The electrode strip includes a substantially inextendible substrate, a plurality of electrode sites, and a region of extensibility between a pair of adjacent electrode sites to allow selective positioning of the electrode sites on a body. The electrode strip further includes a plurality of conductive leads which extend along one surface of the substrate to a different one of the electrode sites.

In a preferred embodiment of the invention, the electrode strip includes an insulating cover layer over the conductive leads. The insulating cover includes a plurality of apertures positioned so that a conductive lead extends at least partially across each of the apertures to form the electrode sites.

In one disclosed embodiment of the invention, each region of extensibility is formed by three transverse folds in the substrate, the folds forming resilient trifold, triangular shaped regions of the substrate between adjacent pairs of apertures to allow adaptive spacing between adjacent apertures. Other illustrative configurations that can be employed as the regions of extensibility are disclosed.

In currently preferred embodiments of the invention, the conductive leads are formed on a substrate of polyester resin. The cover layer is also of polyester resin. Each aperture is connected to a conductive gel pad which has an adhesive surface to contact a body. A protective outer liner is included to protect the adhesive surface of each gel pad prior to attaching the strip to the body.

BRIEF DESCRIPTION OF THE DRAWINGS

The various features and advantages of the invention will be understood in view of the following detailed description taken in conjunction with the following drawings in which:

FIG. 6 is a partial perspective view of a third embodiment of an electrode strip of the present invention;

DETAILED DESCRIPTION

Figure 1:
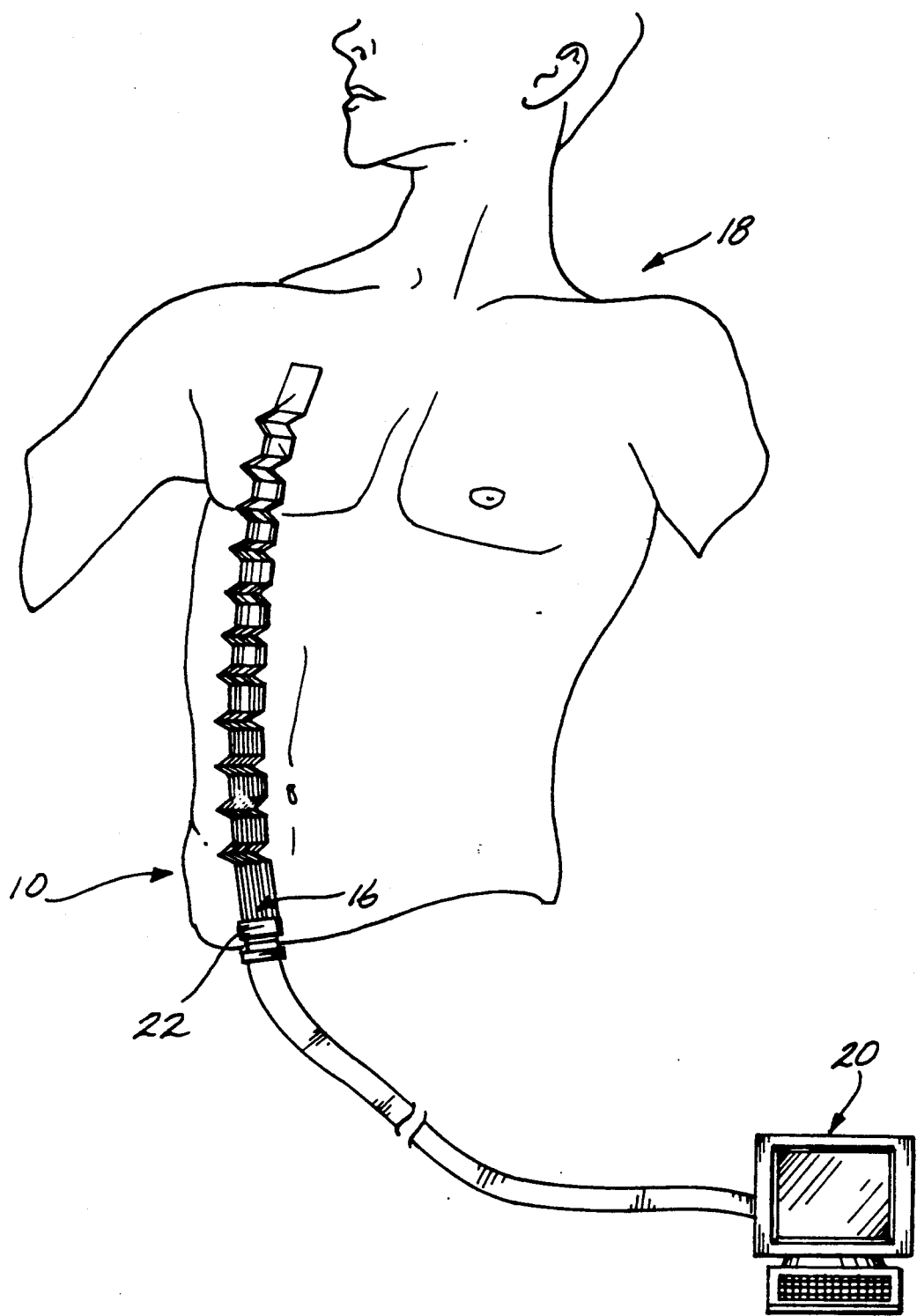
FIG. 1 is a perspective view of an electrode strip of the present invention shown in an operative position on the chest area of a patient.
Figure 2:
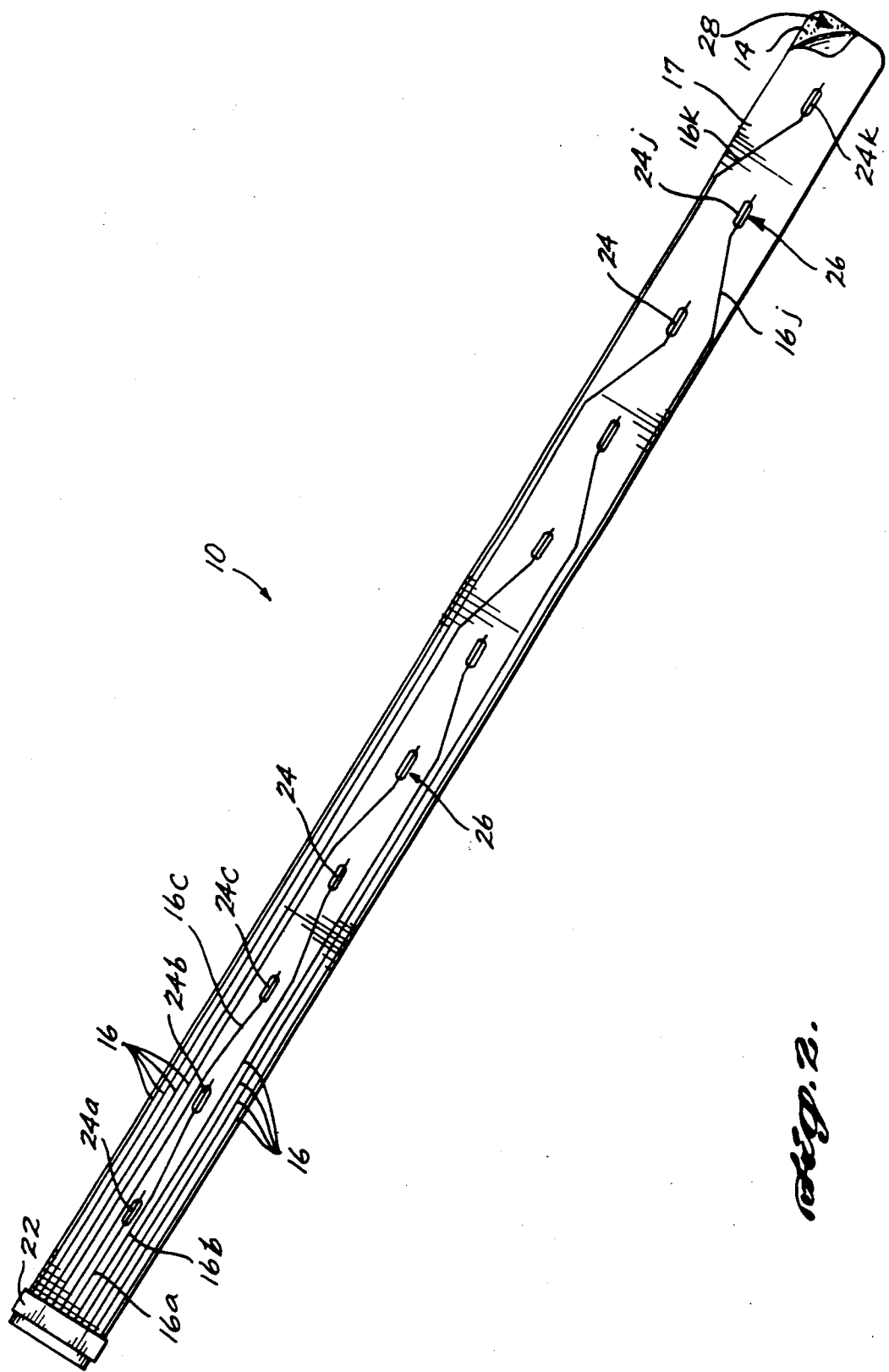
FIG. 2 is a top elevation view of the electrode strip of FIG. 1 prior to formation of regions of extensibility between adjacent apertures.

In accordance with the present invention, the electrode strip provides a relatively inexpensive and potentially disposable device for measuring the activities of the heart and other muscles and organs of a body while including electrodes which can be selectively positioned to accommodate different-sized bodies. With reference to FIG. 2, an electrode strip 10 includes an elongate substrate 14, a plurality of spaced-apart conductive leads (i.e., conductors) 16 that extend along one surface of substrate 14, and an insulating cover layer 17 that insulates all but a portion of each conductive lead 16. With reference to FIG. 1, the leads 16 couple electrical signals between a person 18 and various medical and therapeutic equipment, such as a monitoring device 20, which is generally known in the art. As is shown, one end of electrode strip 10 includes a connector 22 which is configured to mate with a cable extending to the monitoring device 20 or other such equipment.

Figure 3:
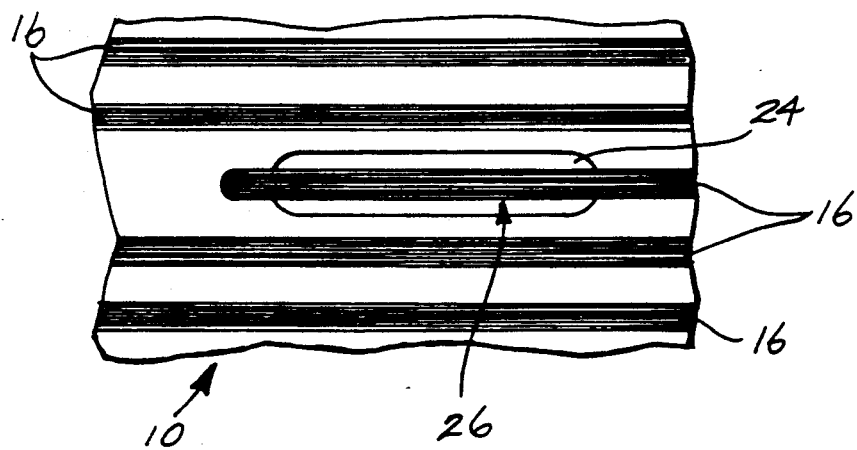
FIG. 3 is an enlarged view of an electrode region (substrate) of the electrode strip shown in FIG. 2.

With reference again to FIG. 2, the cover layer 17 includes a plurality of apertures 24 with each aperture being positioned over a portion of a different one of the conductive leads 16 to allow electrical contact with the body of a person or other living being. In the arrangement of FIG. 3, the depicted aperture 24 is of elongate oval geometry to form an electrode site 26 of corresponding shape. Various other aperture shapes can be employed as long as the associated lead 16 passes partially or entirely across the aperture.

The arrangement of leads 16 as they extend from connector 22 to different ones of the electrode sites 26 may be varied as long as the leads do not overlap one another. In the particular embodiment shown in FIG. 2, the leads are substantially parallel to one another and extend from connector 22 to apertures 24 which are longitudinally spaced apart along the center width of substrate 14. As the leads 16 approach individual apertures 24, they generally taper toward the center width of the substrate to intersect with the apertures. In that regard, the centermost lead 16a terminates at the aperture (24a) nearest the connector 22. Leads 16b and 16c, which lie adjacent the centermost lead 16a, terminate at the two apertures (24b and 24c) which are second and third nearest the connector 22. The pairing of leads 16 with apertures 24 continues in the arrangement of FIG. 2, such that the outermost leads 16j and 16k terminate at the apertures (24j and 24k) furthest from connector 22.

The electrode strip 10 is constructed by depositing or otherwise forming the leads 16 on a first surface 28 of the substrate 14. In this regard various known processes such as painting, screen printing, vacuum coating or sputtering can be used. The cover layer 17 in which the apertures 24 have been previously cut is then affixed to the first surface 28 of the substrate 14 by means of an adhesive material. As an alternative method of forming the leads 16, the substrate material may be clad with a layer of conductive material in which the leads are formed by conventional photolithographic and chemical etching techniques. Preferably, the substrate 14 and cover layer 17 are formed of a polyester resin such as that commercially available under the trade name Mylar, each being on the order of 3 mils thick.

Figure 4:
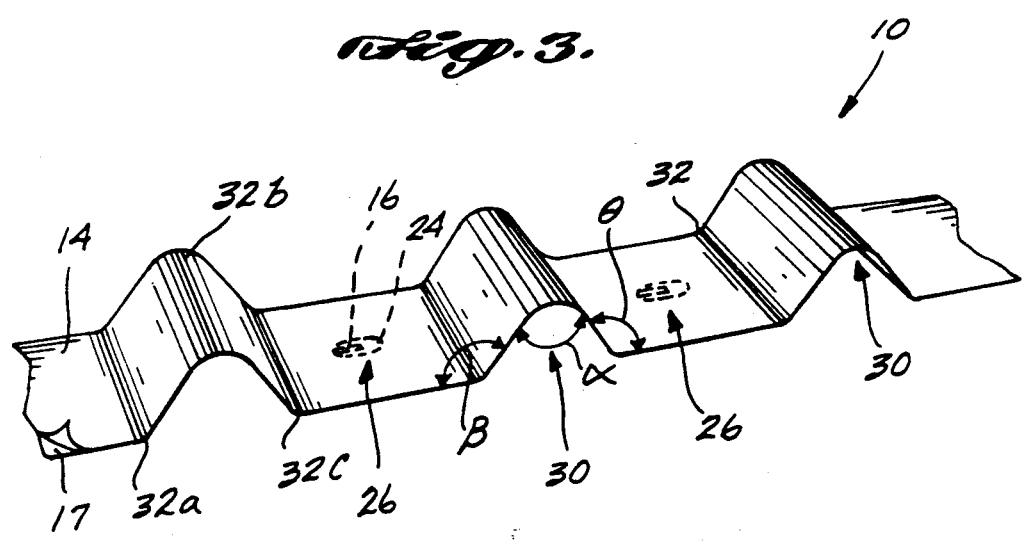
FIG. 4 is a partial perspective view of the electrode strip depicted in FIG. 2 after the electrode strip has been formed to provide regions of extensibility between adjacent apertures.
Figure 5:
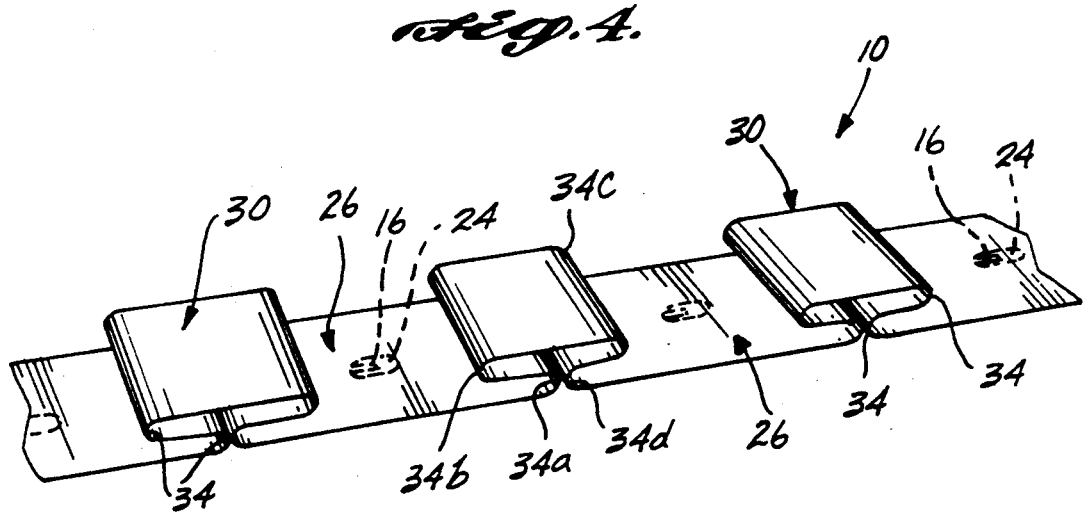
FIG. 5 is a partial perspective view of a second embodiment of an electrode strip of the present invention.

Substrate 14, including the leads 16 and cover layer 17, is flexible but substantially inextendible along its length. A plurality of sections or regions 30 of extensibility are subsequently formed into the substrate between pairs of adjacent electrode sites 26. Illustrative embodiments of the regions of extensibility 30 are shown in FIGS. 4–6. The formation of materials of the type employed in substrate 14 and cover layer 17 is generally understood by those skilled in their use.

The regions of extensibility 30 are formed into the strip 10 by (1) pre-shaping the strip using a jig, mandrel or other device; (2) heating the strip while in the preshaped position and (3) cooling the strip.

An illustrative formation process for the strip 10 involves clamping the strip 10 to a mandrel having a plurality of triangular-shaped sections similar to those illustrated in FIG. 4; immersing the strip in hot water at a temperature between, for example, 180°–212° F.; immersing the strip in cool water, for example, between 45°–60° F.; and, removing the strip from the mandrel. With regard to FIG. 5, each region can be formed by the same process using a jig in place of the mandrel. The jig includes four posts wherein each post causes a 180° turn in the strip 10 when the strip is wrapped around the jig. As can be appreciated, for this process to be used, the substrate 14 (and cover layer 17) must be thermally formable. The optimal parameters of the formation process are dependent upon the particular material used in substrate 14 and cover layer 17.

The resultant regions of extensibility 30 are resilient and extendible sections between adjacent electrode sites 26 on the otherwise inextendible substrate 14. Thus, although the electrode sites 26 are normally separated by predefined distances, the application of longitudinal force to the substrate 14 and regions of extensibility 30 allows the electrode site separation to be altered. As a result, the strip 10 is easily adapted to individual body shapes and sizes while remaining an integral unit.

With reference to FIG. 4, in a first embodiment, each region of extensibility 30 is a tri-fold, triangular-shaped section of substrate 14 formed by three transverse curves or folds 32a, 32b, and 32c. When in the unextended, quiescent state, the geometry of one of the regions 30 roughly parallels that of an isosceles triangle. The angle $\alpha$ of the fold forming the peak of the arc 32b (i.e., the angle opposite the base of the isosceles triangle) is less than 60° with the angles $\beta$ and $\theta$ of the adjacent folds (32a and 32c) being less than 120° each. The angle $\alpha$ of fold 32b will increase (i.e., approach or exceed 60°) when the electrode strip is in effect stretched to increase the distance between adjacent electrode sites 26, conversely, the angle $\alpha$ will decrease to less than 60° when the adjacent electrode sites 26 are moved toward one another. The angles of each fold 32 described offer a desirable degree of extendibility for each region of extensibility 30.

With reference to FIG. 5, in a second embodiment, each region of extensibility 30 includes four transverse folds 34 which collectively form a stubby T-shaped section of substrate 14. More particularly, each fold 34 represents a 180° turn in the substrate. The first fold 34a and fourth fold 34d collectively form the vertical portion of the T, respectively. The folds 34b and 34c form the horizontal portion of the T.

With reference to FIG. 6, in a third embodiment, each region of extensibility 30 includes two opposing spiral wound regions 36. Each spiral wound region 36 is formed by doubling a section of substrate 14 over onto itself and coiling the doubled-over region into a spiral having at least a half turn. In the embodiment of FIG. 6, the spirals forming each region of extensibility have on the order of two and one-half turns. The spiral wound regions 36 of a particular region of extensibility 30 will tend to unwind as the electrode strip 10 is in effect stretched to increase the distance between adjacent electrode sites 26.

The degree of adjustment that can be made to the spacing between adjacent electrode sites 26 is dependent, first upon the distance between adjacent apertures 24, and second by the shape, size and complexity of the regions of extensibility 30. In general, these factors can be varied during both the manufacturing and forming processes of the strip 10 to tailor the strip to any desired application. For example, the embodiment of FIG. 6 may be useful in some situations because the relatively large amount of substrate 14 within each spiral wound region 36 allows a great deal of latitude (in separation) when positioning the electrode sites 26 on a body.

The strip 10 can also be tailored by selecting the number of electrode sites to accommodate specific needs. As another example, a precordial strip requires six electrode sites. To allow strip 10 to properly adjust to the general population in a precordial application, the regions of extensibility 30 are configured to provide a longitudinal adjustment on the order of one centimeter between adjacent electrode sites 26. Further, the nonlinear nature of the anatomically defined electrode locations for precordial monitoring requires that the first and fourth regions of extensibility 30 (from connector 22) be formed to allow both longitudinal and curvilineal adjustment of that area of the strip. A strip could be constructed in accordance with the invention to meet these constraints by, for example, employing folds whose geometry varies across the width of the strip 10 or by employing a nonlinear substrate 14.

Figure 7A:
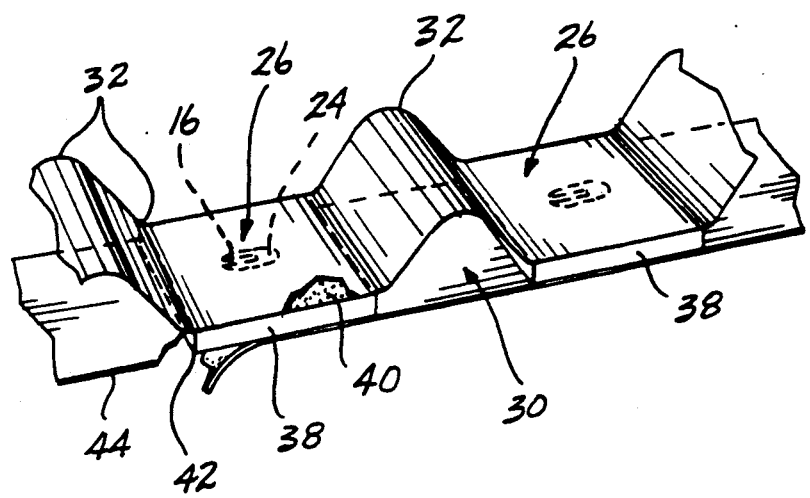
FIG. 7A is a partial perspective view of the electrode strip of FIG. 1 illustrating the use of an adhesive conductive gel pad to interface the electrode strip with the body of a person.

With reference to FIG. 7A, the leads 16 must be electrically coupled to the body of a person or other being (i.e., in signal communication with the body). One method of establishing this electrical contact is through a plurality of conductive gel pads 38 associated with the various electrode sites 26. Thus, the electrode sites 26 do not directly contact the skin. Rather, the conductive leads 16 terminating at each electrode site 26 are coupled to the skin via the gel pads 38. Each pad has adhesive properties on both oppositely disposed surfaces-an upper surface 40 to attach the gel pad 38 to the strip 10 and a lower surface 42 to detachably mount the pad to the body of a person (not shown). Adhesive, electrically conductive gels in this form are generally known in the art.

Once mounted to a person, the entire lower surface 42 of the gel pads 38 will provide electrical conductivity between the person's skin and the conductive leads 16. Thus, it is the area of the lower surface 42 and not the size of the electrode site 26 which most significantly determines the impedance of the electrode/patient interface. This property allows the apertures 24 and the conductive leads 16 to have a relatively small size without affecting the strength of the signals monitored by the end equipment, e.g., the monitoring device 20 shown in FIG. 1.

A desirable skin surface area to obtain electrode readings is on the order of one square inch (i.e., 2.54 square centimeters). Preferably, the strip 10 is provided with one-inch-square gel pads 38 which are pre-attached to the area surrounding each electrode site 26. An outer liner 44 protecting the adhesive on the lower surface 42 of the pads 38 can then be removed just prior to attaching the strip to the body. In one embodiment, shown in FIG. 7A, the protective outer liner 44 is a single strip which covers the lower surfaces 42 of all of the gel pads 38. In this embodiment, removal of the single liner 44 will expose the lower surface 42 of each gel pad 38 for placement on the body.

Figure 7B:
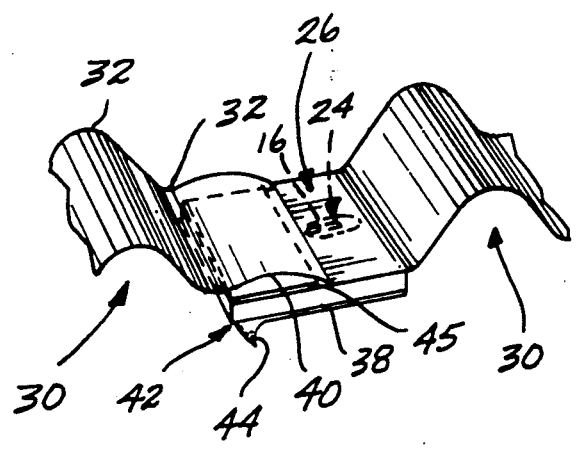
FIG. 7B is a partial perspective view of the electrode strip of FIG. 7A where the ends of each pad opposite the electrode contact with the strip are allowed to remain free of attachment to the strip.

With reference to FIG. 7B, a second method of attaching the gel pads 38 to the electrode strip 10 is illustrated. When applied to a person's body (not shown), longitudinal extension of the strip 10 tends to cause the regions of the substrate 14 around the electrode sites 26 to bend away from the body, i.e., presenting a concave surface to the person's body. To accommodate such bending while maintaining electrical contact between the body and the electrode sites 26, only a portion of the conductive gel pad 38 is attached to the electrode site 26. More specifically, one end of the upper surface 40 of the gel pad 38 is adhesively attached to the substrate 14 at the aperture 24. The remaining portion of the upper surface 40 of gel pad 38, adjacent the electrode site 26, includes a strip 45 of paper or other suitable material that prevents it from adhering to the electrode strip. The entire lower surface 42 of the gel pad 38 is still attached to the person's body. When the gel pad 38 is adhesively joined to the person's body it effectively couples electrical signals to and from the body while still allowing the electrode site 26 to bend away from the body. As previously noted, the protective outer liner 44 applied to the adhesive regions on the lower surface 42 must be removed prior to attaching the pad 38. Where adhesion of the pads 38 to sites 26 is limited by the strips 45, it will be noted that removal of the outer liner 44 must proceed starting from the end of strip 10 opposite to the limited adhesion end of pads 38.

Figure 8:
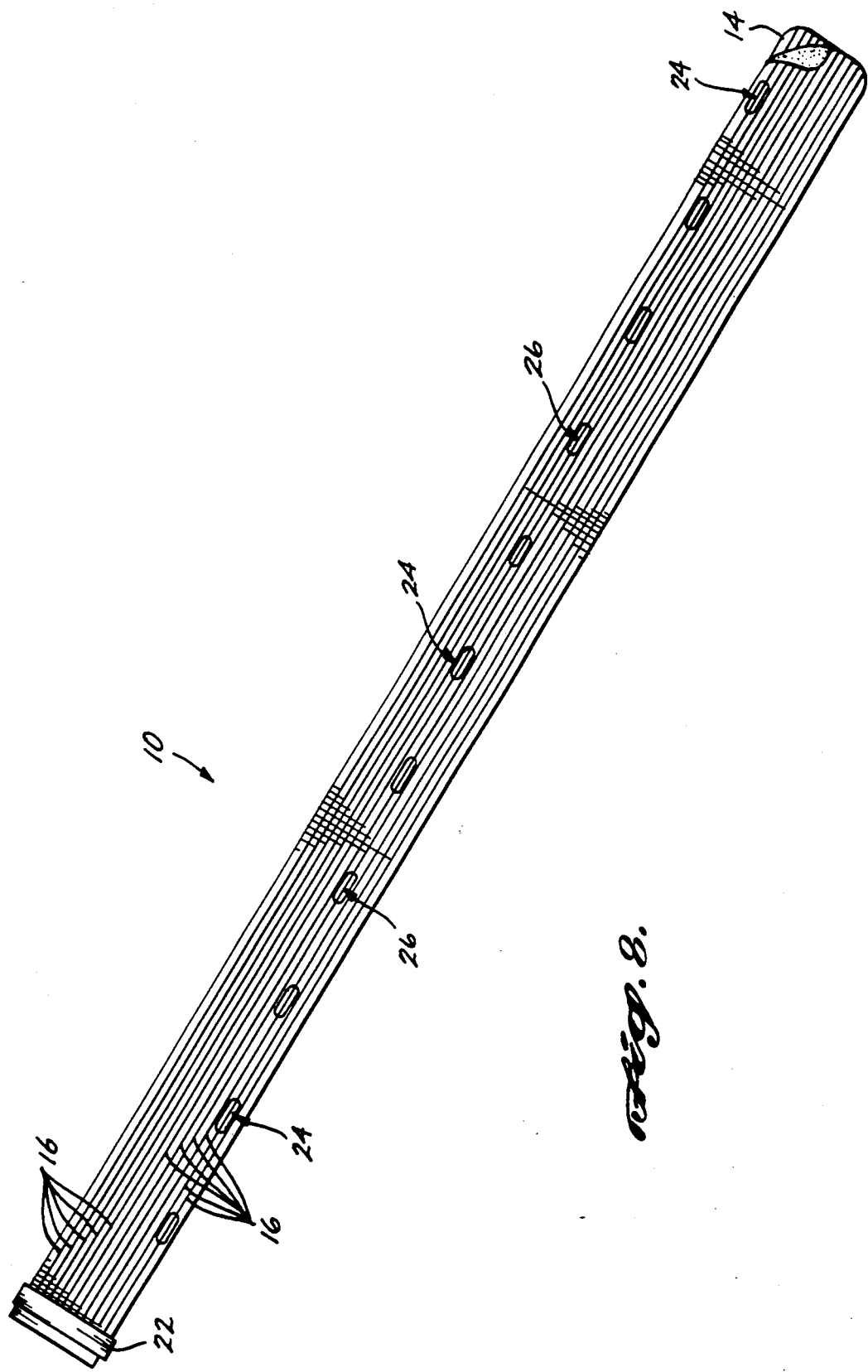
FIG. 8 is a top view of an electrode strip substrate which includes an alternative pattern of apertures, and hence, electrodes.

As is discussed above, the arrangement of the conductive leads 16 as they extend to the apertures 24 is not of critical importance. With reference to FIG. 8, in an alternative arrangement, each conductive lead 16 extends substantially the entire length of the substrate 14, rather than having the individual leads terminate after reaching an aperture as in FIG. 2. In this arrangement, the conductive leads 16 are substantially parallel to one another and to the length of the strip 10. The leads 16 are equally spaced apart across the width of the strip. The corresponding apertures 24 associated with the conductive leads 16 are located at varying widths along the strip 10 and thus are not in longitudinal alignment with the strip as are the apertures of FIG. 2. However, it should be noted that this arrangement of apertures 24, and hence electrode sites 26, will not cause electrode placement problems with respect to the person's skin because the gel pads 38 are longitudinally aligned with the strip 10 and it is the gel pads and not the actual electrode sites 26, which contact the skin (as described above).

The alternative arrangement of leads and apertures in FIG. 8 allows the substrate 14 and leads 16 to be manufactured in a continuous process with adjustments of the apertures' locations in the cover layer facilitating particular applications of the strip. For example, some applications may require the apertures to be spaced further apart or, conversely, closer to one another. This is accomplished with the arrangement of FIG. 8 simply by adjusting the longitudinal spacing between the apertures. In contrast, the embodiment shown in FIG. 2 may require an adjustment in lead layout, as well as aperture positions, to alter the substrate 14 for different applications.

Figure 9:
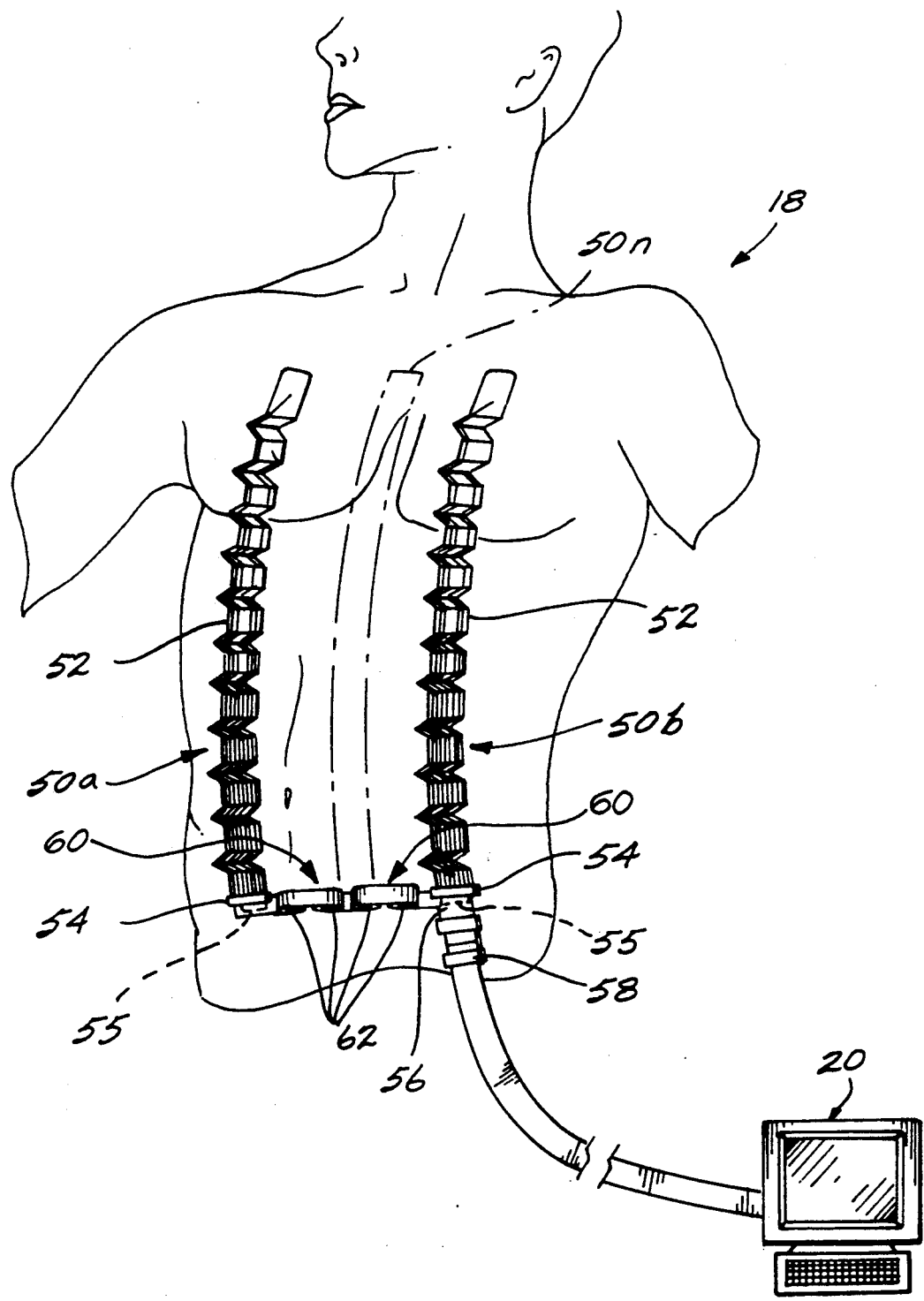
FIG. 9 is a perspective view of a number of electrode strips of the present invention shown in an operative position on the chest area of a patient.

Body surface potential mapping techniques often require the placement of a large number of electrodes to a person in an arrangement comprising any number of columns and rows. With reference to FIG. 9, an exemplary arrangement including a number of columns of electrodes is shown. Each column includes an electrode strip. In that regard, a first electrode strip 50a is illustrated on the right side of the person 18 and a second electrode strip 50b is illustrated on the person's left side. An electrode strip 50n (shown in phantom) representing the nth strip attached to the person is also illustrated. The electrode strips 50 are substantially similar to the electrode strip 10 of FIG. 1. In that regard, each electrode strip 50 includes a plurality of spaced-apart conductors 52 and a connector 54 at an end thereof.

The electrode strips 50 are joined through their connectors 54 to a plurality of connectors 55 in a connector strip 56. The connectors 54 of the electrode strips 50 cooperatively interact with the connectors 55 of the connector strip 56 to couple electrical signals therebetween. Further, the connector strip 56 includes a plurality of spaced-apart conductive leads (not shown) which couple electrical signals between the conductive leads 52 (and, hence, the person 18) and the monitoring device 20. As is shown, the connector strip 56 includes a cable connector 58, which is configured to mate with a cable extending to the monitoring device 20 or other such equipment.

The connector strip 56 utilizes the technology of the present invention to allow flexibility in the placement of the electrode strips 50. To this end, the connector strip 56 includes a number of extensible regions 60 similar to the extensible regions 30 of the electrode strip 10. Preferably, the extensible regions 60 each include two opposing spiral wound regions 62 similar to the spiral wound regions 36 of FIG. 6.

As can be appreciated, the number of strips so depicted in FIG. 9 can be increased to provide a larger number of readings. Further, the length, width and shape of the connector strip 56 can be adjusted to accommodate the number and arrangement of strips employed.

It should be recognized by those skilled in the art that various modifications and changes can be made in the disclosed embodiments of the invention without departing from the spirit and scope of the invention. For example, those skilled in the art will recognize that there are a number of other conductive lead-aperture arrangements which could be employed in accordance with the present invention. Therefore, the scope of the invention should be determined solely by reference to the following claims.

The embodiments of the invention in which an exclusive property or privilege is claimed are defined as follows:

1. An electrode strip for placement on a body, comprising:
    a substantially inextendible substrate having first and second surfaces, a plurality of electrode sites on the first surface of the substrate, and a region of extensibility defined in the substrate between a pair of adjacent electrode sites to allow selective positioning of the adjacent electrode sites on the body; and
    a plurality of spaced-apart conductive leads that extend along the first surface of the substrate to a different one of the electrode sites.

2. The electrode strip of claim 1, further comprising an insulating cover layer that extends over the conductive leads and the first surface of the substrate, the cover layer including a plurality of apertures positioned therethrough so that a conductive lead extends at least partially across each one of the apertures to form the electrode sites.

3. The electrode strip of claim 2, wherein each region of extensibility includes four transverse folds in the substrate, with each fold being on the order of 180°, said folds forming a resilient and approximately T-shaped region in the electrode strip between said pair of adjacent electrode sites.

4. The electrode strip of claim 2, wherein each said region of extensibility includes two counterrotating spirally wound regions of the substrate, said spirally wound regions tending to unwind as the separation between the apertures on each side of each region is increased.

5. The electrode strip of claim 2, wherein each region of extensibility includes three transverse folds which form a tri-fold, triangular-shaped region in the substrate between said pair of adjacent electrode sites.

6. The electrode strip of claim 2, wherein the substrate is elongate and the conductive leads extend longitudinally from a first end of the substrate to the apertures in the insulating cover layer.

7. The electrode strip of claim 6, wherein each region of extensibility includes four transverse folds in the substrate, with each fold being on the order of 180°, said folds forming a resilient and approximately T-shaped region in the electrode strip between said pair of adjacent electrode sites.

8. The electrode strip of claim 6, wherein each region of extensibility includes two counterrotating spirally wound regions of the substrate, said spirally wound regions tending to unwind as the separation between the apertures on each side of each region is increased.

9. The electrode strip of claim 6, wherein the conductive leads extend substantially the entire length of the substrate.

10. The electrode strip of claim 1, including means for coupling the conductive leads to the body, said means comprising a plurality of adhesive conductive gel pads, each of the gel pads coupling a different one of the conductive leads to the body.

11. The electrode strip of claim 10, wherein each conductive gel pad includes an upper surface to contact the substrate and means for preventing a portion of the upper surface from attaching to the substrate to allow the electrode strip to bend away from the conductive gel pad.

12. An assembly of electrodes for placement on a body, comprising:
a plurality of electrode strips, each strip comprising a substantially inextendible substrate having first and second surfaces, a plurality of electrode sites the first surface of the substrate and a region of extensibility between a pair of electrode sites to allow selective positioning of the adjacent electrode sites on the body;
a plurality of spaced-apart conductive leads that extend along the first surface of the substrate of each electrode strip to a different one of the electrode sites on the associated electrode strip; and
means, including a plurality of spaced-apart conductive leads, for joining each of the electrode strips.

13. The assembly of claim 12, wherein each electrode strip further includes an insulating cover layer that extends over the conductive leads and the first surface of the substrate, the cover layer including a plurality of apertures positioned therethrough so that a conductive lead extends at least partially across one of the apertures to form the electrode sites.

14. The assembly of claim 13, wherein the regions of extensibility of at least one of the electrode strips include four transverse folds in the substrate of the electrode strip, with each fold being on the order of 180°, said folds forming a resilient and approximately T-shaped region in the electrode strip between said pair of adjacent electrode sites.

15. The assembly of claim 13, wherein the substrate of each electrode strip is elongate and conductive leads extend longitudinally from a first end of the substrate to the apertures in the insulating cover layer.

16. The assembly of claim 12, wherein the means for joining includes a region of extensibility between a pair of adjacent electrode strips to allow selective positioning of the electrode strips on the body.

17. The assembly of claim 12, wherein each electrode strip includes a connector and the means for joining includes a plurality of connectors which cooperatively interact with the connectors of the electrode strips to couple electrical signals between the means for joining and each electrode strip.

18. An electrode strip, comprising:
a substantially inextendible substrate, including a first end and a lower surface;
an insulating layer covering the lower surface of the substrate, said insulating layer including a plurality of longitudinally spaced-apart apertures extending through the insulating layer;
a plurality of conductors positioned between the substrate and the insulating layer, with each conductor extending from the first end of the strip to one of the apertures;
means, defined in said substrate, for resiliently separating the apertures.

19. The electrode strip of claim 18, wherein said means for resiliently separating the apertures includes a plurality of laterally extending folds in the substrate, the folds forming resilient triangular-shaped regions of substrate between pairs of adjacent ones of the apertures to provide adaptive spacing of the apertures.

20. The electrode strip of claim 18, wherein said means for resiliently separating the apertures includes two spiral wound regions of the substrate, a first region being counterclockwise in rotation and a second region being clockwise in rotation, said regions having a tendency to unwind as the apertures on each side of said means for resiliently separating are separated.

21. The electrode strip of claim 18, wherein said means for resiliently separating the apertures includes four approximately 180° folds between pairs of adjacent ones of the apertures, said folds collectively resembling a T-shaped section of the substrate that provide adaptive spacing of the apertures.

22. The electrode strip of claim 18, wherein the substrate is elongate and each conductive lead extends substantially the entire length of the substrate.

23. The electrode strip of claim 18, including means for coupling the conductive leads to the body, said means comprising a plurality of adhesive conductive gel pads, each of the gel pads coupling a different one of the conductive leads to the body.

24. The electrode strip of claim 23, wherein each of the conductive gel pads includes an upper surface to contact the substrate and means for preventing a portion of the upper surface from attaching to the substrate to allow the electrode strip to bend away from the conductive gel pad.

* * * * *

UNITED STATES PATENT AND TRADEMARK OFFICE
CERTIFICATE OF CORRECTION

PATENT NO. : 5,191,886
DATED : March 9, 1993
INVENTOR(S) : D. S. Paeth et al.

It is certified that error appears in the above-identified patent and that said Letters Patent is hereby corrected as shown below:

| COLUMN | LINE | |
|---|---|---|
| 9 (Claim 12 | 31 Line 5) | after "sites" insert --on-- |

Signed and Sealed this

Twenty-eighth Day of June, 1994

*Attest:*

BRUCE LEHMAN

*Attesting Officer*     *Commissioner of Patents and Trademarks*